(12) United States Patent
Ji et al.

(10) Patent No.: US 6,896,658 B2
(45) Date of Patent: May 24, 2005

(54) SIMULTANEOUS MULTI-MODE AND MULTI-BAND ULTRASONIC IMAGING (75) Inventors: Ting-Lan Ji, San Jose, CA (US); Glen McLaughlin, Saratoga, CA (US)

(73) Assignee: Zonare Medical Systems, Inc., Mountain View, CA (US)

( * ) Notice: Subject to any disclaimer, the term of this patent is extended or adjusted under 35 U.S.C. 154(b) by 460 days.

(21) Appl. No.: 10/039,862

(22) Filed: Oct. 20, 2001

(65) Prior Publication Data

US 2003/0078497 A1 Apr. 24, 2003

(51) Int. Cl.[7] .................................................. A61B 8/00
(52) U.S. Cl. ....................................................... 600/440
(58) Field of Search ................................. 600/443, 447, 600/454–459, 458, 440–441, 437; 128/916; 73/602, 625–626

(56) References Cited

U.S. PATENT DOCUMENTS

| | | | |
|---|---|---|---|
| 4,398,540 A | 8/1983 | Takemura et al. | |
| 4,409,982 A | 10/1983 | Plesset et al. | |
| 4,803,990 A | 2/1989 | Bonnefous et al. | |
| 4,853,904 A | 8/1989 | Pesque | |
| 5,119,342 A | 6/1992 | Harrison, Jr. et al. | |
| 5,140,558 A | 8/1992 | Harrison, Jr. et al. | |
| 5,278,757 A | 1/1994 | Hoctor et al. | |
| 5,291,090 A | 3/1994 | Dias | |
| 5,295,485 A | 3/1994 | Shinomura et al. | |
| RE35,148 E | * 1/1996 | Lizzi et al. ................ | 348/163 |
| 5,483,963 A | 1/1996 | Butler et al. | |
| 5,505,203 A | 4/1996 | Deitrich et al. | |
| 5,667,373 A | 9/1997 | Wright et al. | |
| 5,722,412 A | 3/1998 | Pflugrath et al. | |
| 5,740,806 A | 4/1998 | Miller | |
| 5,793,701 A | 8/1998 | Wright et al. | |
| 5,817,024 A | 10/1998 | Ogle et al. | |
| 5,839,442 A | 11/1998 | Chiang et al. | |
| 5,893,363 A | 4/1999 | Little et al. | |
| 5,897,501 A | 4/1999 | Wildes et al. | |
| 5,904,652 A | 5/1999 | Gilbert et al. | |
| 5,905,692 A | 5/1999 | Dolazza et al. | |
| 5,908,389 A | * 6/1999 | Roundhill et al. .......... | 600/443 |
| 5,919,138 A | 7/1999 | Ustuner | |
| 5,925,967 A | 7/1999 | Toda | |
| 5,964,709 A | 10/1999 | Chiang et al. | |
| 5,970,025 A | 10/1999 | Cole et al. | |
| 5,973,438 A | 10/1999 | Toda | |
| 6,055,861 A | 5/2000 | Banta, Jr. et al. | |
| 6,063,030 A | 5/2000 | Vara et al. | |
| 6,089,096 A | 7/2000 | Alexandru | |
| 6,113,545 A | 9/2000 | Chiao et al. | |
| 6,126,608 A | 10/2000 | Kemme et al. | |
| 6,135,961 A | 10/2000 | Pflugrath et al. | |
| 6,139,498 A | 10/2000 | Katsman et al. | |
| 6,174,286 B1 | 1/2001 | Ramamurthy et al. | |

(Continued)

OTHER PUBLICATIONS

U.S. Appl. No. 09/860,209, filed May 18, 2001, Mir Imran, Miniaturized Ultrasound Apparatus and Method.

(Continued)

*Primary Examiner*—Francis J. Jaworski
(74) *Attorney, Agent, or Firm*—Carr & Ferrell LLP (57) ABSTRACT

An ultrasound imaging method and system configured to simultaneously acquire and process multi-mode and multi-band echo information from a single set of pulse firings is provided. Raw ultrasound signals are digitized and stored in an I/Q data buffer. The stored data are then parallel preprocessed as a function of frequency band or alternative encoding. Parallel preprocessing optionally includes manipulating the data in respect to different imaging modes. Outputs of the parallel preprocessors are coupled to separate echo formers used to simultaneously reconstruct various desired echo information to form a multi-mode or multi-band image. The echo formation process is optionally performed in parallel.

19 Claims, 6 Drawing Sheets

U.S. PATENT DOCUMENTS

| | | |
|---|---|---|
| 6,203,498 B1 | 3/2001 | Bunce et al. |
| 6,238,346 B1 | 5/2001 | Mason |
| 6,251,073 B1 | 6/2001 | Imran et al. |
| 6,514,206 B2 * | 2/2003 | Maxwell et al. ............ 600/443 |
| 6,695,783 B2 * | 2/2004 | Henderson et al. ......... 600/443 |

OTHER PUBLICATIONS

U.S. Appl. No. 09/872,541, filed May 31, 2001, Glen McLaughlin, System and Method for Phase Inversion Ultrasonic Imaging.

U.S. Appl. No. 10/039,858, filed Oct. 20, 2001, Umit Tarakci, A System and Method for Acoustic Imaging at Two Focal Lengths with a Single Lens.

U.S. Appl. No. 10/039,910, filed Oct. 20, 2001, Umit Tarakci, System and Method for Coupling Ultrasound Generating Elements to Circuitry.

U.S. Appl. No. 10/039,922, filed Oct. 20, 2001, Xufeng Xi, Block Switching in Ultrasound Imaging.

U.S. Appl. No. 29/147,576, Ian Felix, Handheld Ultrasonic Display Device, Aug. 31, 2001.

U.S. Appl. No. 29/147,660, Ian Felix, Handheld Ultrasonic Display Device with Cover, Aug. 31, 2001.

U.S. Appl. No. 29/148,421, Ian Felix, Handheld Ultrasonic Transducer with Curved Bulb Grip, Sep. 19, 2001.

U.S. Appl. No. 29/148,532, Ian Felix, Handheld Ultrasonic Transducer with Bulb Grip, Sep. 19, 2001.

U.S. Appl. No. 29/149,730, Ian Felix, Docking Station, Oct. 15, 2001.

* cited by examiner

SIMULTANEOUS MULTI-MODE AND MULTI-BAND ULTRASONIC IMAGING

CROSS-REFERENCES TO RELATED APPLICATIONS

This application is related to U.S. patent application Ser. No. 10/039,922 entitled "Block Switching in Ultrasound Imaging," filed on Oct. 20, 2001. The subject matter of this related application is incorporated herein by reference. The related application is commonly owned and assigned.

BACKGROUND

1. Field of the Invention

The invention is in the field of imaging devices and more particularly in the field of ultrasonic imaging.

2. Description of the Prior Art

Ultrasonic imaging is a frequently used method for examining a wide range of materials. The method is especially common in medicine because of its relatively non-invasive nature, low cost, and fast diagnostic cycles. Typically, ultrasound imaging is accomplished by generating and directing ultrasonic sound waves into a material under investigation and then observing reflections generated at the boundaries of dissimilar materials. The reflections are converted to electrical signals by receiving devices (transducers) and then processed, using beam-forming techniques known in the art, to determine the locations of echo sources. The resulting data is displayed using a display device such as a monitor.

Typically, the ultrasonic signal transmitted into the material under investigation is generated by applying continuous or pulsed electronic signals to a transducer. The transmit frequency of medical ultrasound is most commonly in the range of 1 MHz to 15 MHz. The ultrasound propagates through the material under investigation and reflects off of structures such as boundaries between adjacent tissue layers. As it travels, the ultrasonic energy may be scattered, resonated, attenuated, reflected, or otherwise modified. Portions of the reflected signals are returned to the transducers and detected as echoes. The detecting transducers convert the echo signals to electronic signals and furnish them to a beamformer. The beamformer calculates locations of echo sources and typically includes simple filters and signal averagers. Calculated positional information, produced through a serial series of beam-forming operations, is used to generate two-dimensional data that can be presented as an image. In prior art systems, the rate at which images are formed (the frame rate) is limited by at least the pulse return time. The pulse return time is the time between the transmission of ultrasonic sound into the media of interest and the detection of the last reflected signals.

As an ultrasound pulse propagates through a material under investigation, additional harmonic frequency components are generated. These additional harmonic frequency components continue to propagate and, in turn, reflect off of or interact with other structures in the material under investigation. Both fundamental and harmonic signals are detected. The analysis of harmonic signals is generally associated with the visualization of boundaries or image contrast agents designed to re-radiate ultrasound at specific harmonic frequencies.

Several modes of ultrasonic imaging are established in the prior art. These prior art modes include analyzing signals at the fundamental (base-band) or harmonic frequencies for studying static structures in the material under investigation, and detecting movement using spectral Doppler or color Doppler imaging modes. These imaging modes are either sequentially or alternatively executed and the results combined in a single image. For example, in one prior art system a first series of ultrasound pulses is first fired to facilitate tissue harmonic imaging that is utilized to examine a human heart. A second series of ultrasound pulses is fired to generate color Doppler imaging signals at a fundamental frequency. These signals measure the velocity of blood flow through the heart. The first series and second series of ultrasound pulses are alternated in a line-interleaved or frame-interleaved manner. The signals generated by each series are analyzed separately and the resulting two-dimensional data is combined in a single data set for display to the user. In the display it is common to use color to differentiate and characterize the combined data sets. Since the data are recorded using two different sets of ultrasound pulses, generated at different times, the displayed image may contain undesirable temporal anomalies. For example, such an anomaly could indicate blood flow through a closed heart valve. Also, using multiple series of pulses exposes the material under investigation to additional ultrasound energy. This additional energy may be considered undesirable.

SUMMARY OF THE INVENTION

The present invention includes systems and methods for performing parallel and multi-mode processing of ultrasound signals. For example, one method of parallel processing ultrasound signals is ultrasonic imaging including the steps of transmitting ultrasound pulses into a media of interest that modifies the ultrasound pulses, receiving the modified ultrasound pulses at a sensor, generating signals responsive to the received ultrasound pulses using the sensor, processing the signals using a plurality of imaging modes; interpreting the processed signals to generate responsive positional data; and generating image data with no visible temporal anomalies using the positional data. Such an image is said to be visibly temporally synchronized.

This method can be performed using an ultrasonic imaging system including an ultrasound transducer for transmitting ultrasound pulses into a media of interest that modifies the ultrasound pulses, a sensor (which is optionally the same transducer used for transmitting) for receiving the modified ultrasound pulses and generating analog signals responsive to the modified ultrasound pulses, an A/D converter for converting the analog signals to digital data, a plurality of frequency band preprocessors for preprocessing the digital data in parallel, and an echo-forming system for interpreting the preprocessed digital data and generating positional data responsive to the preprocessed digital data. The echo-forming system optionally includes an area-forming system, a volume-forming system, or a multidimensional-forming system.

DETAILED DESCRIPTION OF THE PREFERRED EMBODIMENT

Figure 1:
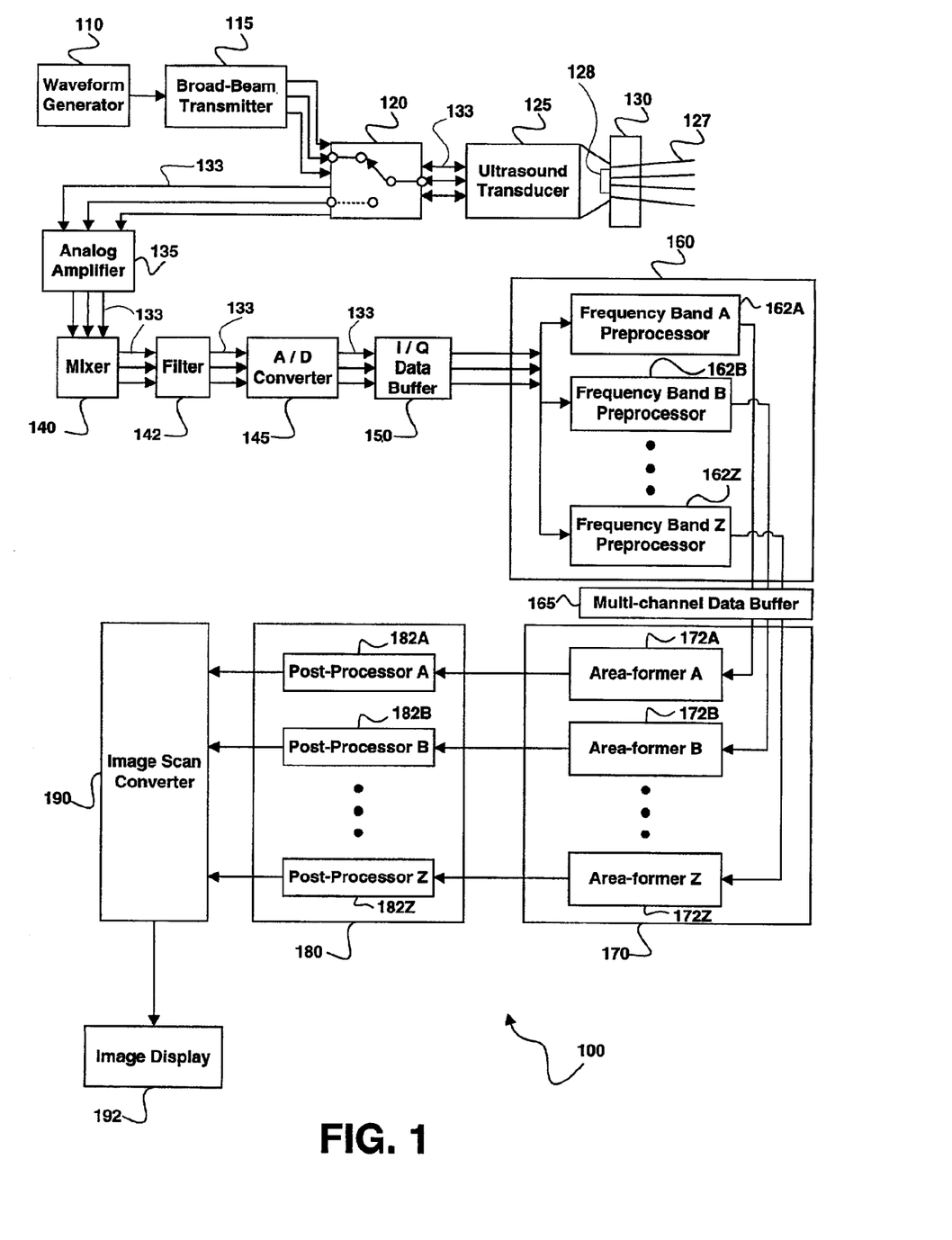
FIG. 1 is a block diagram of an embodiment of the invention.

FIG. 1 is a block diagram showing an embodiment of the invention generally designated system 100. System 100 includes a waveform generator 110 that produces waveforms having a plurality of pulses. These pulses are optionally of differing or multiple frequencies. The output of waveform generator 110 is coupled to a broad-beam transmitter 115. Broad-beam transmitter 115 splits the input waveform into multiple channels, amplifies the signal, and/or applies the delays required to form a broad-beam ultrasound wave. Broad-beam technology reduces the number of transmitted pulses required to image an area and enables use of area-forming techniques in place of prior art beam-forming methods. In an alternative embodiment broad-beam transmitter 115 is replaced by a prior art beam transmitter. The output of broad-beam transmitter 115 is coupled through a multi-channel transmit/receive switch 120 and used to drive an ultrasound transducer 125. Ultrasound transducer 125 sends ultrasound pulses 127 into a media of interest 130. These ultrasound pulses 127 are modified through attenuation, scattering, reflection, harmonic generation, or the like. Returning echoes are received by transducer elements 128. Transducer elements 128, which are used to detect echoes, may be a part of ultrasound transducer 125, used to generate ultrasound pulses 127. The detected signals include ultrasound with frequencies near the original transmitting frequency as well as with other harmonic frequencies. Each of transducer elements 128 converts the received ultrasound pulses into electrical signals and couples these electrical signals to a distinct data channel 133.

After conversion to electrical signals, pulses are coupled to multi-channel transmit/receive switch 120 from distinct data channels 133. Transmit/receive switch 120 directs the electrical signals to a multi-channel analog amplifier 135. Analog amplifier 135 amplifies the signals and couples them to a mixer 140 for demodulation. Mixer 140 can be an analog mixer, a multi-channel mixer, a phase modulator, a time signal multiplier and/or any other signal modulator known in the art. The demodulated signals are made up of in-phase and quadrature (I/Q) components. Each distinct data channel 133 is independently coupled through a filter 142.

In one embodiment filter 142 includes a multi-channel band-pass filter that selectively impedes specific frequency ranges. In this embodiment, the resulting signals are digitized using a multi-channel A/D (analog to digital) converter 145 and are stored in an I/Q data buffer 150. I/Q data buffer 150 is multi-channel and can optionally be programmed to individually sum digitized signals received from each distinct data channel 133. I/Q data buffer 150 makes the stored data available to a preprocessing module 160. In an alternative embodiment, a digital mixer 140 and/or digital filter 142 are optionally placed after A/D converter 145.

An embodiment of preprocessing module 160 includes a plurality of frequency band preprocessors 162A–Z. These labels are arbitrary designations and not intended to limit the number of frequency band preprocessors 162 to twenty-six. Each frequency band preprocessor 162 can process multiple data sets, from several or all of the distinct data channels 133, stored in I/Q data buffer 150. The frequency band preprocessors are optionally differentiated by one or more characteristics. These differentiating characteristics include, for example, the processing frequency range (frequency band), specific encoding within the processed signal, the mode of processing preformed, or the like. Signals, resulting from one or more transmit/receive cycles, are optionally combined, filtered, decoded, and/or modulated, prior to image formation. In one embodiment of the present invention, each frequency band preprocessor 162A–Z within preprocessing module 160 can access all or part of the data within I/Q data buffer 150. The frequency band preprocessors 162A–Z may each take selected data and process it in parallel such that all of the data passed by band-pass filter 142 is optionally processed by at least one frequency band preprocessor 162A–Z. The preprocessed, multi-band, multi-channel signals are optionally stored in multi-channel data buffer 165 and made available to a series of area-formers 172 within an area-forming module 170. In FIG. 1 area-formers 172 are individually designated 172A–Z. These labels are arbitrary designations and not intended to limit the number of area-former 172A–Z to twenty-six.

Embodiments of area-forming module 170 processes data stored in multi-channel data buffer 165, or delivered directly from preprocessing module 160. The processing performed by area-forming module 170 includes calculating positional information regarding the source of signals within the media of interest 130. Each of area-former 172A–Z is capable of forming positional information covering an area using broad-beam technology, rather than just positional information along a line. Because preprocessing module 160 pre-processes the data, each of area-formers 172 optionally operates on a data set restricted to a specific criterion or processed to accentuate a specific aspect of the data. For example, in one embodiment area-former 172A receives data preprocessed to identify moving components within media of interest 130. Area-former 172A, therefore, may operate on Doppler components of the total signal received by preprocessing module 160. In the same embodiment, area-former 172B is disposed to process data combined after processing by frequency band preprocessors 162A and 162B, each of which preprocesses data with a specific encoding. When input data is processed in parallel, each area-former 172A–Z generates output data with the same time zero and temporal characteristics and the output data is temporally synchronized. Because preprocessing module 160 optionally reduces the total amount of data, area-forming module 170 may operate on only part of the data received by preprocessing module 160 and calculations may, thus, be performed more rapidly. Data prepared by preprocessing module 160 are parallel processed by area-forming module 170. The parallel aspect of the processing eliminates temporal delays between the outputs of the area-forming module 170 and allows different types of imaging modes to be simultaneously executed. For example, data accentuating motion can be processed in one imaging mode at the same time that data representing static structures is processed in another imaging mode.

In an embodiment output of area-forming module 170 is combined, or further processed, in a post-processor system 180. Since the outputs of area-forming module 170 can be based on signals recorded at substantially the same time, the output data, which can result from several imaging modes, are combined without introducing temporal jitter. In various aspects of the invention post-processor system 180 also combines data from multiple broad-beam zones and prepares a single data set for delivery to an image scan converter 190 for output on an optional image display 192.

Figure 2:
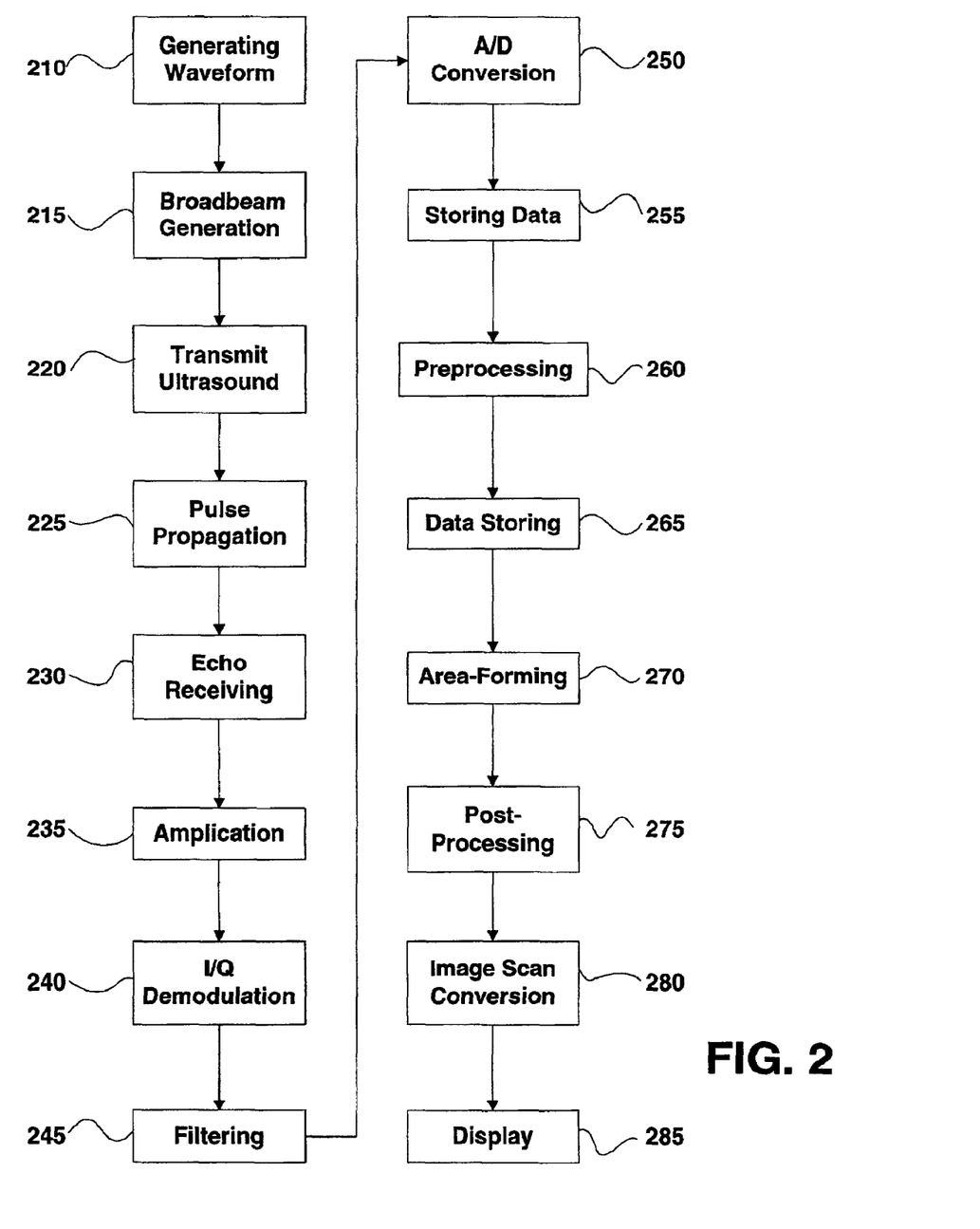
FIG. 2 is a flow diagram showing steps of an embodiment of the invention.
Figure 3:
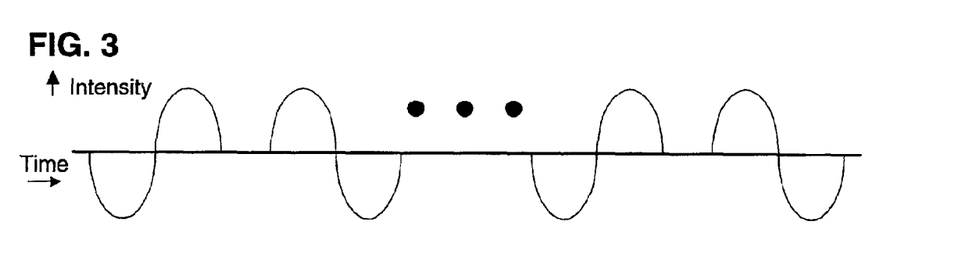
FIG. 3 shows illustrative waveforms representing signals found at a step in the execution of an embodiment of the invention.

FIG. 2 is a flow diagram showing steps of an embodiment of the invention utilizing the system illustrated by FIG. 1. In a waveform generation step 210 waveform generator 110 is used to produce a waveform having a series of pulses. These pulses are grouped as singlets, pairs, or larger combinations of pulses. The waveform generated in waveform generation step 210 optionally includes a plurality of characteristics such as frequencies, amplitudes, pulse widths, phases, or variation thereof. These characteristics are optionally used to encode the waveform. As an example, FIG. 3 illustrates the waveform including a series of pulse pairs having opposite phase.

In a broad-beam generation step 215, broad-beam transmitter 115 processes the waveform generated by waveform generator 110. In various aspects of the invention the processing by broad-beam transmitter 115 includes amplifying the waveform, separating the waveform among distinct data channels 133, applying delays and weightings to each distinct data channel 133, and the like. Broad-beam generation step 215 further effectuates coupling the processed waveform within each distinct data channel 133 to multi-channel transmit/receive switch 120 and to multi-element ultrasound transducer 125. In a transmit ultrasound step 220 each element of ultrasound transducer 125 emits ultrasound pulses 127 using the processed waveforms. Since the present invention optionally includes broad-beam technology, the number of pulses required to cover the imaging area can be significantly fewer than the number required to cover a similar area using conventional beamforming methods known in the art.

In pulse propagation step 225, ultrasound pulses 127 propagate through media of interest 130. Variations in media of interest 130 cause echoes to be generated and ultrasound pulses 127 to be altered. In an echo receiving step 230, returning ultrasound signals are received by ultrasound transducer 125 using transducer elements 128. Transducer elements 128 receive the returning ultrasound signals at the frequency near or at the frequencies of ultrasound pulses 127 and/or at harmonics thereof. Each receiver generates signals in at least one of distinct data channel 133 and the signals of each distinct data channel 133 are coupled through transmit/receive switch 120 to analog amplifier 135. From echo receiving step 230 through a post-processing step 275 all operations are optionally performed on distinct data sets, such as set distinguished by different analysis modes, in parallel.

Figure 4A:
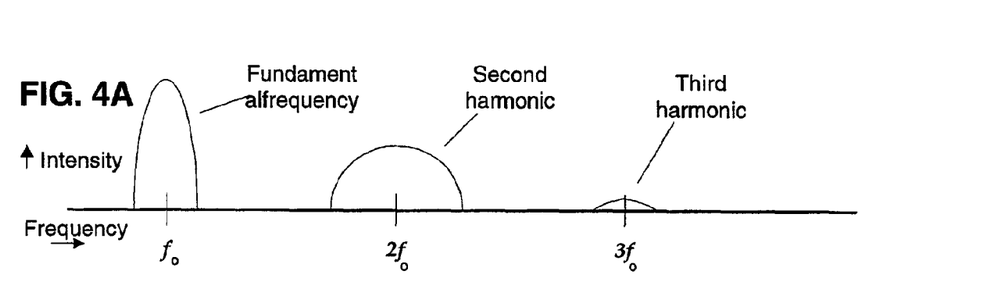
FIG. 4A shows an example of a demodulated signal spectrum from a single channel associated with a single receiving transducer.
Figure 4B:
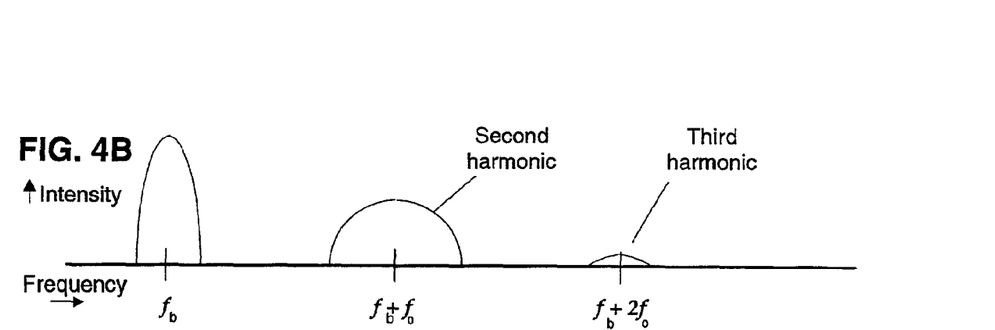
FIG. 4B shows an illustrative spectrum representing signals found after demodulation by an I/Q mixer.

An amplification step 235 uses a low-noise analog amplifier 135 to amplify distinct data channel 133 signals. In an I/Q demodulation step 240, each channel is processed by mixer 140 that demodulates the signals. FIG. 4A illustrates an example of a resulting demodulated signal spectrum from a single channel associated with a single receiver. Signal components can be found near the frequency ($f_0$) at which the ultrasound was transmitted and at harmonics of the transmitted frequency ($2f_0$, $3f_0$, or the like). In an embodiment of the invention, mixer 140 demodulates the components of the signal at the fundamental frequency ($f_0$) to a base-band frequency ($f_b$) and demodulates the $2^{nd}$ harmonic components of the signal to a new frequency ($f_b+f_0$). The result is illustrated in FIG. 4B. In a filtering step 245 each signal is optionally coupled through filter 142. Filter 142 applies a high-pass, low-pass, or band-pass filter to the signal. The type of filtering is selected as a function of the expected use of the signal.

In an A/D conversion step 250 the signal in each distinct data channel 133 is converted from the analog to the digital domain by A/D converter 145. In an alternative embodiment A/D conversion step 250 occurs prior to demodulation step 240 or filtering step 245. In a data storage step 255, the digitized data from each channel is stored in I/Q data buffer 150. I/Q buffer 150 optionally sums the digital signals resulting from a plurality of pulses. The summed, "raw," data is sampled at the output of the I/Q data buffer 150. Under selected summation and phase conditions, the summation process results in an average approaching zero for some components of the signals.

In a data preprocessing step 260, preprocessing module 160 reads data from I/Q data buffer 150 and processes it using one or more of frequency band preprocessors 162A–Z Each frequency band preprocessor 162A–Z can access all of the data available in I/Q data buffer 150. However, depending on the type of imaging mode desired, each frequency band preprocessor 162A–Z can also be operated to process only a segment of the data. In various aspects of the invention, these segments are divided by transducer channel, frequency range, or encoding. In various embodiments, frequency band preprocessors 162A–Z apply a variety of processing routines to the data. In an illustrative example, half of the frequency band preprocessors 162A–Z are configured to process data associated with Doppler signals while the other half are configured to process signals associated with static structures. Thus, in these embodiments, preprocessing module 160 processes the data stored in I/Q data buffer 150 in multiple modes, in multiple frequency bands, with multiple encodings, and/or in multiple independent data channels. Since preprocessing module 160 consists of multiple independent frequency band preprocessors 162A–Z, processing can occur in parallel.

In an embodiment of the invention signals are processed by frequency band pre-processors 162A–Z as a function of encoding included within the signal. For example, if waveform generator 110 produces pulses at two or more distinct frequencies, the returned (encoded) ultrasound echoes can be differentiated (decoded) by their frequency. This ability to differentiate allows pulses to be sent into the material under investigation at a rate faster than un-encoded pulses, since a second set of pulses can be sent before the first is received. Using this encoding the pulse transmit rate and the collection of data is not limited by the roundtrip time of a pulse. The pulse roundtrip time is the time between transmission of a pulse and the detection of all resulting echoes. Frequency band preprocessors 162A–Z can be individually arranged to select and process signals resulting from one or more of distinct frequency bands.

After preprocessing, data is optionally stored in multichannel data buffer 165 in a data storing step 265. This step enables further data manipulation, such as averaging and synchronization between preprocessing module 160 and area-forming module 170. If the product of the number of preprocessing modes, frequency bands, and data channels is larger than the number of frequency band pre-processors then some of the channels can be preprocessed in parallel and the results are stored in multi-channel data buffer 165. Following this preprocessing process, another set of channels is optionally preprocessed and stored. The preprocessing process can be repeated until all channels have been preprocessed and stored. The use of multi-channel data buffer 165 further enables the implementation of a larger number of parallel preprocessing modes, frequency bands, encoding, and the like.

In an area-forming step 270 preprocessed data is used to perform parallel area-forming calculations using area-forming module 170. Area-forming module 170 includes a plurality of area-former 172A–Z, Each area-former 172A–Z can be enabled to identify locations of echo sources from data generated by an individual frequency band preprocessor 162A–Z, For example, in an embodiment of the present invention, area-former 172A is configured to process data preprocessed by frequency band preprocessor 162A. In another embodiment of the invention, area-former 172A is configured to process data combined in multi-channel data buffer 165 after parts of the data are separately preprocessed by frequency band preprocessor 162B and frequency band preprocessor 162A. Preprocessing the data potentially reduces noise, undesirable signal components, and the total amount of data within each data channel.

The existence of several area-former 172A–Z within area-forming module 170 enables parallel processing of data associated with multiple imaging modes. For example, in one embodiment area-former 172A is configured to process data associated with moving echo sources and area-formi er 172B is configured to process data associated with static echo sources. In another embodiment area-former 172A is configured to process data with encoding type A and area-former 172B is configured to process data with encoding type B, where encoding types A and B are any two distinguishable encoding schemes.

In an optional post-processing step 275 the output of area-forming module 170 is post-processed by post-processing system 180. Post-processing can include one or more elements such as encoding of data generated using different modes, sum and difference calculations between data generated using different modes, calculation of differences among data recorded at different times, differential and integral calculations, or the like. Post-processing system 180 can also combine data derived from multiple transmit zones to produce data sets covering an expanded area. Post-processing generates at least data representing some attribute of the signal as a function of a coordinate system.

In an optional image scan conversion step 280 an image is prepared using image scan converter 190. The image optionally includes motion video and/or false color representations of the encoding developed in post-processing step 275. For example, in one embodiment of the invention velocities of detected materials are calculated and colors are chosen so as to visually convey the range and distribution of velocities. In another embodiment of the invention static components of the material of interest are shown using a color scheme designed to show material ultrasound reflectivity.

The above process is optionally repeated for multiple transmit zones until an entire field of view is covered. For example, see co-pending U.S. patent application Ser. No. 10/039,922 entitled "Block Switching in Ultrasound Imaging" that published on Feb. 5, 2004 as U.S. Patent Publication No. US 2004-0024316 A1. The final images of multi-mode and/or multi-band signals are combined and scan-converted to an appropriate display format by image scan converter 190.

In an optional display step 285 the image prepared in image scan conversion step 280 is displayed using image display 192. The final images are displayed with little or no time delay or time lag between various components of the image that result from different imaging mode or frequency bands.

In the present invention more than one imaging mode is optionally performed on a single set of data produced from a single set of transmitted ultrasound pulses. In these embodiments a single set of ultrasound pulses, are used in parallel to generate echo location data based on multiple analysis modes. In several embodiments, parallel multi-mode imaging creates a visibly temporally synchronized image, thereby eliminating time jitter (temporal anomalies) associated with prior art methods of serial generation of echo data in multi-rode imaging. Multi-band preprocessing and area-forming enables the separation of signals based on encoding characteristics. For example, images, or other echo location data, produced from separate frequency bands can be formed in parallel and compounded together to decrease speckle noise without reduction of frame rate.

Figure 5:
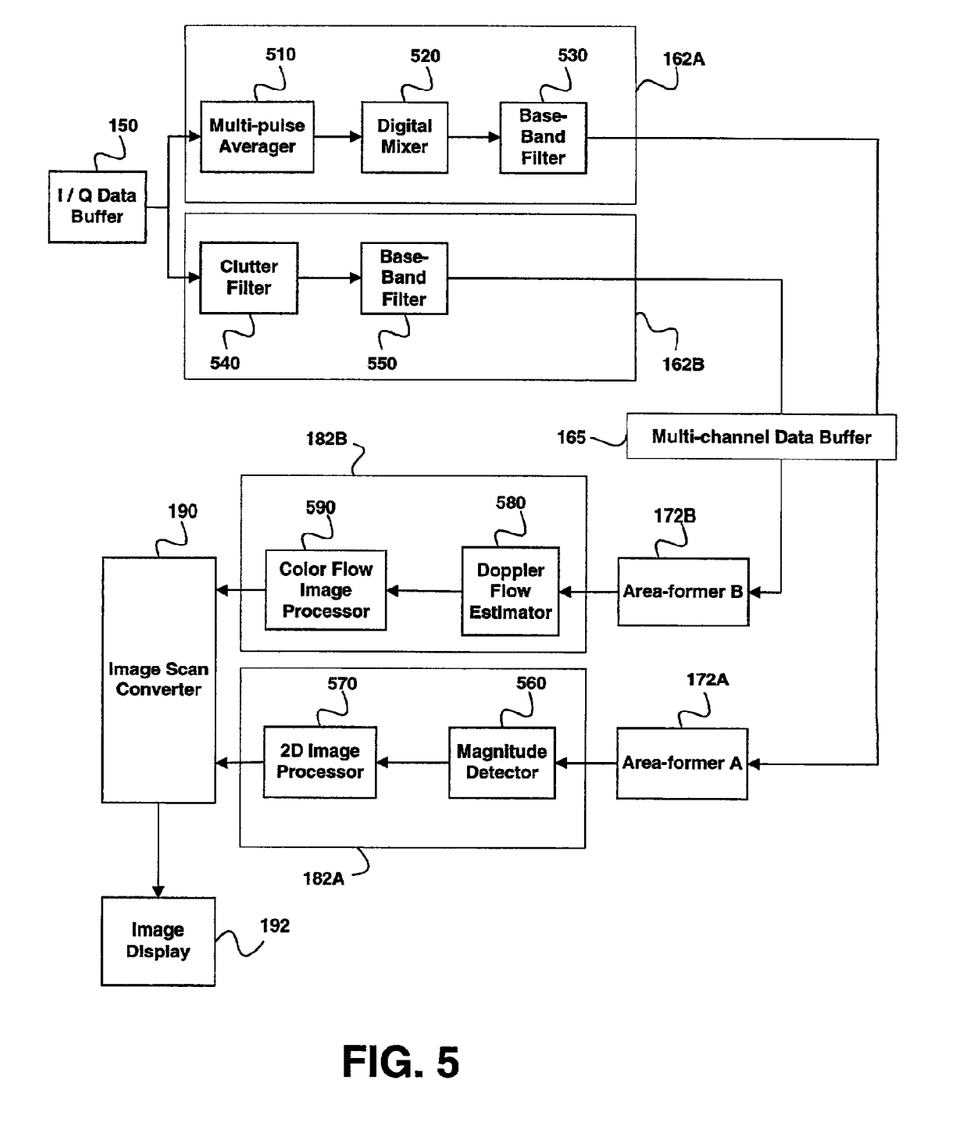
FIG. 5 is a block diagram showing an embodiment of the invention wherein harmonic signals for 2D imaging and fundamental signals for Doppler imaging are processed in parallel.

FIG. 5 is a block diagram showing an embodiment of the invention wherein harmonic signals for 2D imaging and fundamental signals for color Doppler imaging are produced and processed in parallel. This embodiment executes the two different data processing modes at the same time. In the illustrative example of FIG. 5, one of the modes is designed to perform high-resolution 2D harmonic tissue imaging, while the other mode is designed to perform color Doppler flow imaging. Both modes use the same set of data that are produced from a series of pulse firings and collected at I/Q data buffer 150. Alternative embodiments optionally include more than two different analysis modes executed in parallel.

In the 2D harmonic tissue imaging mode, data is copied from I/Q buffer 150 to frequency band preprocessor 162A. In this mode, frequency band preprocessor 162A is used to process harmonic signals to produce a high resolution 2D tissue image. Frequency band preprocessor 162A is configured to include multi-pulse averager 510, digital mixer 520, and base-band filter 530. The results of the preprocessing are optionally stored in multi-channel data buffer 165 and coupled to area-former 172A to reconstruct echo location data (image). The echo location data (image) is coupled to post-processor 182A. In this embodiment, post-processor 182A includes a magnitude detector 560 and 2D image processor 570.

In the Doppler flow imaging mode, data is copied from I/Q buffer 150 to frequency band preprocessor 162B. In this embodiment, this data is the same data copied from I/Q buffer 150 for use in a parallel 2D harmonic tissue imaging mode. In the Doppler flow imaging mode, frequency band preprocessor 162B is configured to include a clutter filter 540 and a base-band filter 550. Using these elements, frequency band preprocessor 162B processes the fundamental frequency signal to detect moving targets within media of interest 130. After optional storage in multi-channel data buffer 165 and processing by area-former 172B, the re-constructed echo location data is coupled to post-processor 182B, which includes a Doppler flow estimator 580 and a color flow image processor 590. Image scan converter 190 combines the echo location data generated using both processing modes and converts the combined data into an appropriate display format to form the final image. The final image is optionally displayed using image display 192.

The various elements 510 through 590 introduced in FIG. 5 are optionally implemented using software. Thus, while preprocessor 162A includes multi-pulse averager 510, digital mixer 520, and base-band filter 530 in one instance of an embodiment, in a subsequent instance of the same embodiment preprocessor 162A may be reconfigured via software to include instead clutter filter 540 and base-band filter 550. Post-processor 182A is optionally configurable through software in an analogous manner.

Figure 6A:
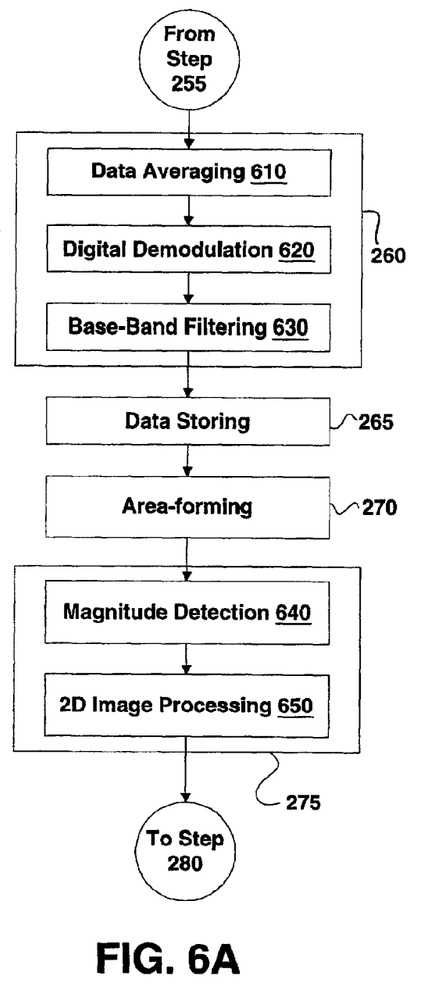
FIG. 6A shows steps involved in a method of the invention wherein harmonic signals are processed for 2D imaging.
Figure 6B:
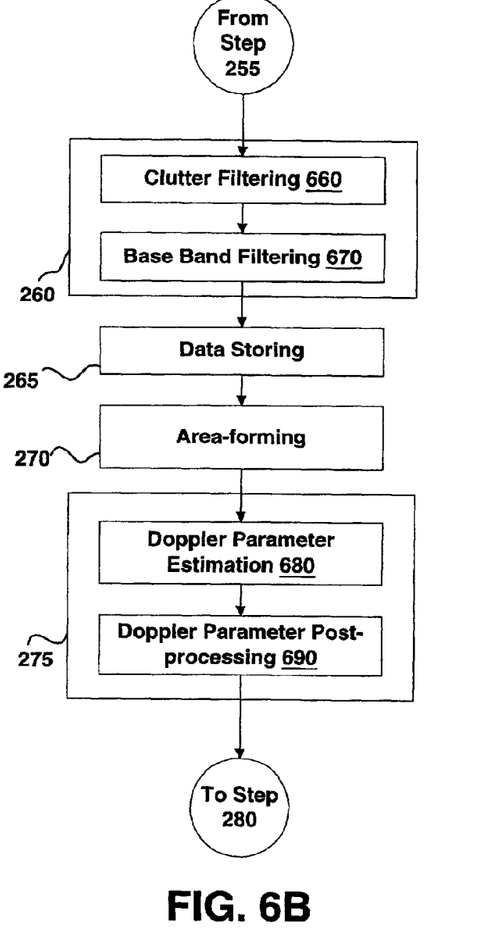
FIG. 6B shows steps involved in a method of the invention wherein fundamental signals are processed for Doppler imaging.

FIG. 6 includes two flowcharts showing processes enabling two different imaging modes that can be executed in parallel utilizing the elements shown in FIG. 5. FIG. 6A shows steps involved in a method of the invention wherein harmonic signals are processed for 2D imaging. FIG. 6B shows steps involved in a method of the invention wherein fundamental signals are processed for Doppler imaging. Both flowcharts start from step 255 and conclude at step 280 of FIG. 2.

Figure 7A:
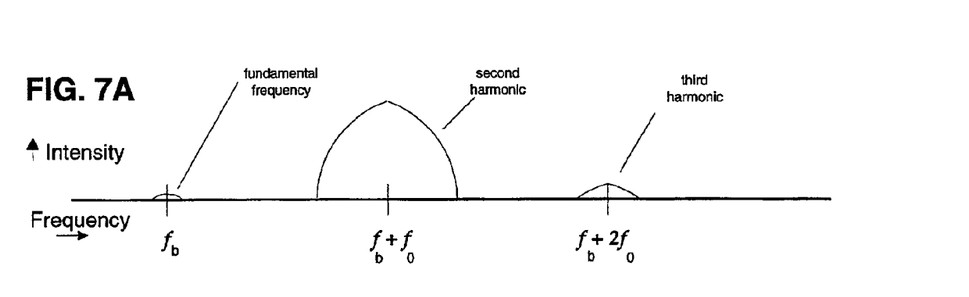
FIG. 7A shows an illustrative spectrum representing signals found after processing using a multi-phase averager.
Figure 7B:
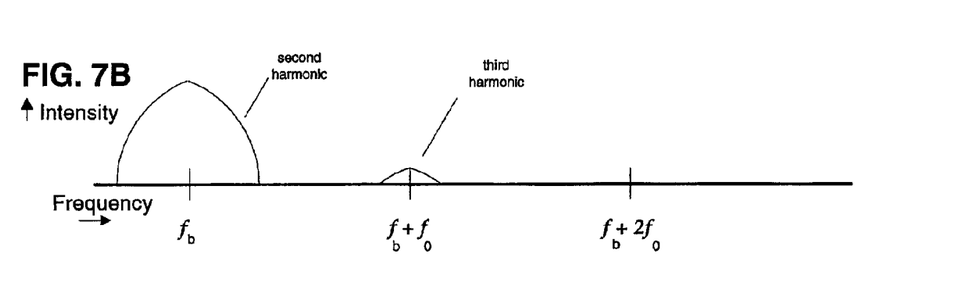
FIG. 7B shows an illustrative spectrum representing signals found after demodulating the signal shown in FIG. 7A using a digital mixer.

In the method illustrated by FIG. 6A, data preprocessing step 260 includes a data averaging step 610, a digital modulation step 620, and a base-band filtering step 630. In data averaging step 610, multi-pulse averager 510 (FIG. 5) reduces or eliminates fundamental frequency components by averaging multiple received signals generated using multiple pairs of phase-inverted transmitting pulses. Since the $2^{nd}$ harmonic component of the received signals from these phase-inverted pulse sequence are in-phase, the signal-to-noise ratio of the $2^{nd}$ harmonic component is enhanced by the averaging process. An illustration of resulting signals is shown in FIG. 7A. Signals at the fundamental frequency are essentially cancelled and the $2^{nd}$ harmonic signals are enhanced. In alternative embodiments wherein the transmitting pulse sequence is not phase-inverted, the signal average simply serves to improve signal-to-noise ratio. In digital demodulation step 620 the digital mixer 520 demodulates the $2^{nd}$ harmonic component down to base-band frequency. Possible resulting signals are illustrated in FIG. 7B. In base-band filtering step 630, base-band filter 530 is used to filter out any residual fundamental frequency component and other noise outside the base-band, while preserving the demodulated $2^{nd}$ harmonic signal.

After base-band filtering step 630, the data are optionally stored, in a data storing step 265, in multi-channel data buffer 165. In an area-forming step 270 the pre-processed $2^{nd}$ harmonic components are coupled to area-former 172A and echo location data is re-constructed for 2D tissue image.

In the method illustrated by FIG. 6A, post-processing step 275 includes a signal magnitude detection step 640 and a 2D image processing step 650. Magnitude detection step 640 includes I/Q signal-to-magnitude conversion and log-compression. 2D image processing step 650 optionally includes operations such as adjustment of gain and dynamic range, spatial and/or temporal filtering, and the like.

In the method illustrated by FIG. 6B, preprocessing step 260 includes a clutter filtering step 660 and a base-band filtering step 670. In clutter filtering step 660, clutter filter 540 is applied to the same multiple signals collected for harmonic tissue imaging to remove signals resulting from stationary and slow-moving sources within the media of interest 130. In base-band filtering step 670, base-band filter 550 is used to extract the clutter filtered fundamental frequency component and remove any noise outside base-band. Preprocess data step 260 is followed by optional store data step 265 and area-forming step 270.

In the method illustrated by FIG. 6B a post-processing step 275 includes a Doppler parameter estimation step 680 and a Doppler parameter post-processing step 690. In Doppler parameter estimation step 680, Doppler flow estimator 580 calculates flow parameters such as Doppler velocity, Doppler velocity variance, Doppler energy, and the like. These calculations are optionally accomplished using auto-correlation methods known in the art. In Doppler parameter post-processing step 690 color flow image processor 590 can use thresholds, noise reduction, smoothing, color coding and/or other image processing techniques to generate a color image conveying information of the Doppler parameters of interest.

The methods illustrated by FIGS. 6A and 6B are optionally performed in parallel. The results of both processes are combined in a single image data set in image scan conversion step 280 (FIG. 2). This single image data set is displayed in display step 285 using image display 192. Since both imaging modes are executed in parallel and use the same set of received data the outputs are generated more quickly than serial execution and the images produced using each imaging mode are temporally synchronized with each other. Quicker image generation enables a higher frame rate. The synchronization of data collection for multiple imaging modes can eliminate or reduce temporal anomalies within a resulting composite image. Encoded data arising from multiple transmitted pulses are optionally added together to improve signal-to-noise ratios.

Steps 260 through 275 optionally include additional and alternative imaging modes such as fundamental imaging, color Doppler imaging, harmonic imaging, spectral Doppler imaging, and/or any other ultrasound imaging mode. Combinations of three or more parallel modes are also possible in alternative embodiments. For example, one set of three parallel modes includes harmonic tissue imaging, color Doppler imaging, and spectral Doppler imaging. Alternatively, another set of three parallel modes includes harmonic tissue imaging, Doppler tissue imaging and color Doppler imaging.

In practice the above methods are optionally applied to a series of zones covering an image field of view within media of interest 130. Each zone can be processed independently and an image of the combined zones can be constructed by image scan converter 190. In each zone a set of N pulses is used to generate data using parallel processing. For K zones a total of K*N pulses are required to form a complete image. For some imaging modes the minimum value of N is two and for other imaging modes the minimum value of N is one. Increasing the number of processing modes does not necessarily increase the number of required pulses. Also, minimizing power consumption extends the lifetime of limited power sources, such as batteries, and enables the use of battery powered, single or multi-mode, instruments with increased operating times.

The parallel processing architecture described in this invention result in very fast data processing speeds. The pre-processing of raw I/Q data optimizes the input signal and improves signal to noise ratios prior to area formation. This optimized input signal improves the quality of area formation and precision of the resulting image data.

From the description of the preferred embodiments of the process and apparatus set forth herein, it will be apparent to one of ordinary skill in the art that variations and additions to the embodiments can be made without departing from the principles of the present invention. For example, preprocessing module 160 and area-forming module 170 can be used for the processing of ultrasound data obtained through alternative means. In various embodiment area formers 172 are replaced by alternative echo-forming systems, such as series of parallel multi-line beamformers, individual examples of which are known in the art. Echo-forming systems include beam-forming systems, area-forming systems, volume-forming systems, and multidimensional-forming systems. The ultrasound system of the present invention may be used to image a wide range of materials.

We claim:

1. A method of using ultrasound to analyze a media of interest, comprising:

transmitting a single set of ultrasound pulse firings into the media of interest, the ultrasound pulse firings being modified by the media of interest;

receiving at a transducer the modified ultrasound pulse firings;

generating signals in response to the received modified ultrasound pulse firings;

parallel processing the signals using a plurality of imaging modes;

generating positional data responsive to the parallel processed signals; and generating image data using the positional data, the image data having no visible temporal anomalies.

2. The method of claim 1, wherein generating positional data includes area-forming.

3. A method of using ultrasound to analyze a media of interest, comprising:

transmitting a single set of ultrasound pulse firings into the media of interest, the ultrasound pulse firings being modified by the media of interest;

receiving at one or more transducers the modified ultrasound pulse firings;

generating analog signals in response to the received modified ultrasound pulse firings;

converting the analog signals to digital data using an A/D converter;

preprocessing the digital data using a plurality of frequency band pre-processors;

generating positional data responsive to the preprocessed digital data; and generating image data using the positional data, the image data having no visible temporal anomalies.

4. The method of claim 3, wherein digital data resulting from an individual member of the single set of ultrasound pulse firings is processed using a plurality of imaging modes.

5. The method of claim 3, wherein preprocessing the digital data is preprocessed in parallel.

6. The method of claim 3, wherein the positional data is generated using echo-forming.

7. The method of claim 3, wherein the positional data is generated using echo-forming and the echo-forming uses an area-forming module that includes a plurality of area-formers.

8. The method of claim 3, further comprising providing preprocessed digital data to one or more members of a plurality of area-formers from one or more members of the plurality of frequency band pre-processors.

9. The method of claim 3, further comprising providing the positional data to an image scan converter, wherein the positional data is generated using a plurality of imaging modes.

10. The method of claim 9, further comprising generating image data using the image scan converter and the positional data.

11. The method of claim 9, further comprising generating image data using the image scan converter and the positional data, wherein the image data is visibly temporally synchronized.

12. The method of claim 3, wherein preprocessing the digital data is performed using a plurality of imaging modes.

13. The method of claim 12, wherein the plurality of imaging modes includes Doppler imaging.

14. The method of claim 12, wherein the plurality of imaging modes includes imaging using harmonic frequencies.

15. The method of claim 3, wherein preprocessing the digital data is done in parallel, and the plurality of frequency band preprocessors are responsive to encoding within the digital data.

16. The method of claim 3, further comprising post-processing the positional data in parallel using a plurality of post-processors.

17. An ultrasonic analysis system comprising:

an ultrasound transducer for transmitting a single set of ultrasound pulse firings into a media of interest such that the media of interest modifies the ultrasound pulse firings;

a transducer for receiving the modified ultrasound pulse firings and generating signals responsive to the modified ultrasound pulse firings;

a plurality of frequency band preprocessors for preprocessing the signals in parallel;

an echo-forming system for generating positional data responsive to the pre-processed signals; and an image converter system for generating image data using the positional data, the image data having no visible temporal anomalies.

18. The system of claim 17, wherein the echo-forming system includes a plurality of beamformers configured to receive signals preprocessed using a plurality of imaging modes.

19. The system of claim 17, wherein the echo-forming system includes an area-forming module.

* * * * *